(12) United States Patent
Verhoeven et al.

(10) Patent No.: US 11,660,018 B2
(45) Date of Patent: May 30, 2023

(54) BREATH ANALYZER, VENTILATOR, AND METHOD FOR BREATH ANALYSIS

(71) Applicant: Loewenstein Medical Technology S.A., Luxembourg (LU)

(72) Inventors: Jan Verhoeven, Ettlingen (DE); Benno Doemer, Ettlingen (DE); Matthias Schwaibold, Karlsruhe (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 363 days.

(21) Appl. No.: 16/937,784

(22) Filed: Jul. 24, 2020

(65) Prior Publication Data
US 2021/0022642 A1  Jan. 28, 2021

(30) Foreign Application Priority Data

Jul. 26, 2019 (DE) .......................... 102019005280.3

(51) Int. Cl.
  *A61B 5/08*  (2006.01)
  *A61B 5/087*  (2006.01)
  (Continued)

(52) U.S. Cl.
  CPC .............. *A61B 5/082* (2013.01); *A61B 5/087* (2013.01); *A61B 5/0816* (2013.01); *A61B 5/091* (2013.01); *A61B 5/4848* (2013.01); *A61B 5/7282* (2013.01)

(58) Field of Classification Search
  CPC ....... A61B 5/082; A61B 5/0816; A61B 5/087; A61B 5/091; A61B 5/4848; A61B 5/7282; A61B 5/0823; A61B 5/085; A61B 5/4836; A61B 5/7264; A61M 2016/0027; A61M 2205/3365; A61M 2230/04; A61M 2230/06; A61M 2230/202; A61M 2230/432; A61M 2230/60; A61M 2230/63; A61M 2230/65; A61M 16/024; A61M 16/00; A61M 2016/0015; A61M 2016/003; A61M 2205/3327; A61M 2205/3334

See application file for complete search history.

(56) References Cited

U.S. PATENT DOCUMENTS

2001/0039950 A1  11/2001  Scholler et al.
2008/0110461 A1  5/2008  Mulqueeny et al.
(Continued)

FOREIGN PATENT DOCUMENTS

DE  102014003542 A1  9/2015
DE  102016013138 A1  5/2018
(Continued)

*Primary Examiner* — Andrey Shostak
(74) *Attorney, Agent, or Firm* — Abel Schillinger, LLP

(57) ABSTRACT

A breath analyzer for detecting breathing events of a person ventilated with a respiratory gas, comprising an electronic computing and storage unit configured to receive a signal corresponding to a ventilation pressure and/or a respiratory flow and/or a tidal volume of the respiratory gas delivered to the person and, during a predetermined analysis duration, to detect a curve of the signal by a curve analyzer. A ventilator for ventilating a person with a respiratory gas, which ventilator comprises the breath analyzer and a method for detecting breathing events of a person ventilated with a respiratory gas is also described.

20 Claims, 9 Drawing Sheets

(51) Int. Cl.
 *A61B 5/091* (2006.01)
 *A61B 5/00* (2006.01)

(56) References Cited

U.S. PATENT DOCUMENTS

| | | | |
|---|---|---|---|
| 2009/0107498 A1* | 4/2009 | Plattner | A61M 16/024 128/204.23 |
| 2011/0060531 A1* | 3/2011 | Sugo | A61B 5/029 702/179 |
| 2012/0037159 A1 | 2/2012 | Mulqueeny et al. | |
| 2015/0258290 A1* | 9/2015 | Landwehr | A61B 5/091 128/202.22 |
| 2018/0126103 A1 | 5/2018 | Kruger et al. | |

FOREIGN PATENT DOCUMENTS

| | | | |
|---|---|---|---|
| EP | 1136094 | A2 | 9/2001 |
| EP | 2216063 | A2 | 8/2010 |
| WO | 2006079152 | A1 | 8/2006 |
| WO | 2010121313 | A1 | 10/2010 |

* cited by examiner

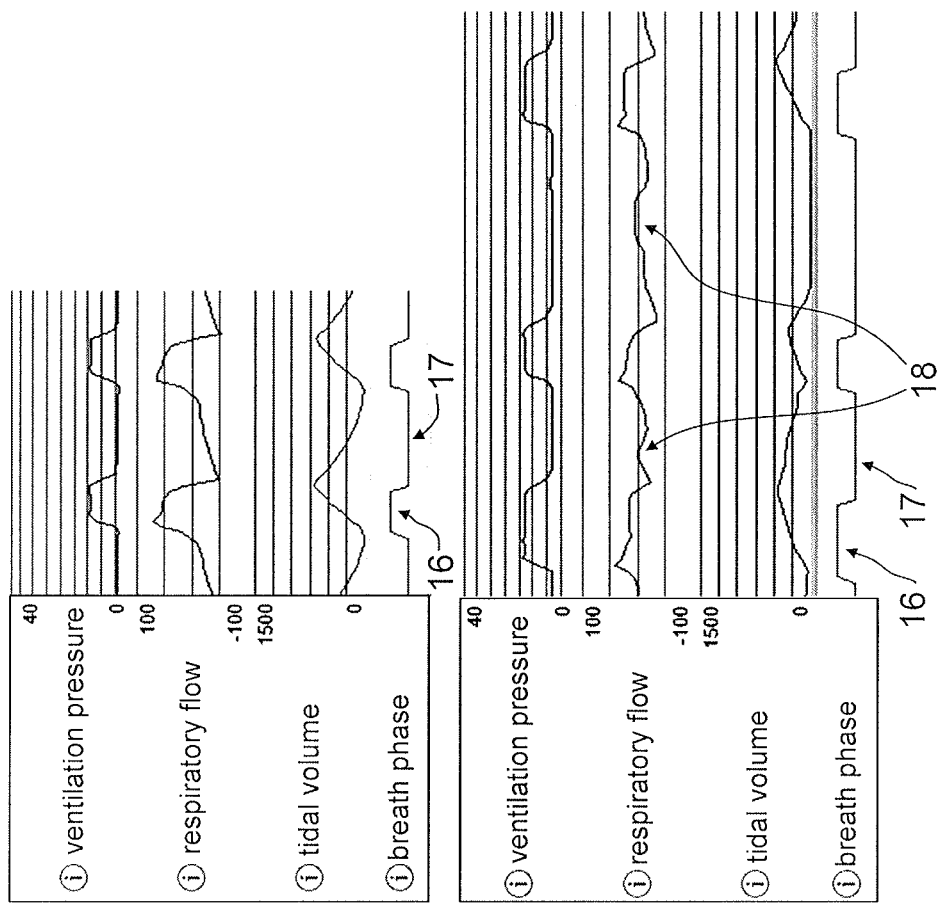

BREATH ANALYZER, VENTILATOR, AND METHOD FOR BREATH ANALYSIS

CROSS-REFERENCE TO RELATED APPLICATIONS

The present application claims priority under 35 U.S.C. § 119 of German Patent Application No. 102019005280.3, filed Jul. 26, 2019, the entire disclosure of which is expressly incorporated by reference herein.

BACKGROUND OF THE INVENTION

1. Field of the Invention

The present invention relates to a breath analyzer for the detection of breathing events of a person ventilated with a respiratory gas for example by a ventilator. The invention further relates to a ventilator for ventilating a person with a respiratory gas, and to a method for detecting breathing events of a person ventilated with a respiratory gas.

2. Discussion of Background Information

In ventilators for ventilating persons with a respiratory gas, it is often advantageous if there is a possibility of detecting breathing disturbances during the ventilation. On the one hand, such detection makes it possible to monitor the efficiency of the ventilation by the ventilator, and, on the other hand, primary and secondary diseases can be better detected. Moreover, the ventilator can be controlled according to the detected breathing patterns or breathing events and adapted (dynamically) and individually to the person who is to be ventilated.

A ventilator with a device for monitoring respiratory parameters is known, for example, from EP 1 136 094 B1, the entire disclosure of which is incorporated by reference herein. By means of a sensor, a time curve of the respiratory parameter to be monitored is detected and made available to an analyzer, which performs a pattern recognition and is coupled to a classifier for evaluation support and to a memory which supplies comparison patterns needed for the pattern recognition.

Against this background, it would be advantageous to have available a breath analyzer for the detection of breathing events of a person ventilated with a respiratory gas, a ventilator for ventilating a person with a respiratory gas, and a method for detecting breathing events of a person ventilated with a respiratory gas, which significantly reduces the time needed to evaluate the breathing events that are detected during a complete analysis period. Moreover, the breath analyzer, the ventilator and the breath analysis method should advantageously be able to be implemented in compact form, using technical means of relatively low complexity, and therefore cost-effectively.

SUMMARY OF THE INVENTION

The present invention provides a breath analyzer a ventilator, and a method for breath analysis as set forth in the instant independent claims. Further particularly advantageous embodiments of the invention are set forth in the respective dependent claims.

It is to be appreciated that the features individually presented in the claims can be combined with one another in any desired, technically meaningful way and show further refinements of the invention. The description additionally characterizes and specifies the invention in particular in conjunction with the drawings.

It also is to be noted that an "and/or" conjunction used herein between two features, and linking them to each other, is always to be interpreted as meaning that in a first embodiment of the subject matter according to the invention only the first feature may be present, in a second embodiment only the second feature may be present, and in a third embodiment both the first and the second feature may be present.

According to the invention, a breath analyzer for the detection of breathing events of a person ventilated with a respiratory gas has an electronic computing and storage unit, which can be embodied for example in the form of a processor-based electronic controller (e.g. micro-processor, microcontroller, DSP, etc.) and at least one electronic memory (e.g. RAM, ROM, EPROM, Flash, magnetic memory, etc.) interacting with the controller. According to the invention, the computing and storage unit is designed and configured to receive a signal, in particular an electronic signal, corresponding to a ventilation pressure and/or a respiratory flow and/or a tidal volume of the respiratory gas supplied to the person and, during a predetermined analysis duration, to detect a curve of the signal (also designated hereinbelow as signal curve) by means of a curve analyzer.

Moreover, the computing and storage unit according to the invention is designed and configured to determine from the determined signal curve (in particular directly after determination thereof) a signal segment which is fixed on the basis of a predefined segment duration or a segment duration detected from the signal curve, wherein the segment duration is considerably shorter than the (total) analysis duration. The analysis duration can be, for example, in the range of several minutes up to one or several hours or even one or several days, whereas the segment duration preferably generally comprises a duration in the range of one or a few seconds to one minute, particularly preferably a maximum of about one, about two or at most about three minutes.

The computing and storage unit is further designed and configured to assign the determined signal segment by means of a comparator to one of several breath classes (herein also designated as assigned/detected breath pattern or also just as breath pattern) and in each case to store a frequency of occurrence, of the breath class assigned (i.e. having occurred) during the analysis duration or the whole analysis period, in a frequency counter provided for each breath class in the storage unit, and to store at least one of the signal segments determined during the analysis duration, but always fewer than the frequency of occurrence detected in the frequency counter (i.e. the total number of detected signal segments of a defined breath class during the whole analysis period), for each assigned (i.e. occurred) breath class in the storage unit. The assigning of the signal segment to a breath class signifies that one or more defined features of the signal curve in the signal segment are identical or at least similar to features of one of the several breath classes.

On the basis of the frequency counter, and even with relatively long analysis periods, for example several hours to several days, it is possible, within a very short time, to establish an assessment from the few but relevant stored analysis results for the ventilated person. Moreover, the frequency counters (even with a large number of different breath classes) require very little in terms of the storage resources that have to be made available. Even if one or a few stored signal segments are added in for each breath class, the overall storage requirement of the breath analyzer according to the invention is still only a fraction of what would be needed for continuous storage of the originally received curve of the signal representing the ventilation pressure and/or the respiratory flow and/or the tidal volume of the respiratory gas supplied to the ventilated person. Moreover, according to the invention, fewer than all of the signal segments detected in the analysis period for one and the same breath class are always stored, such that the assessment on the basis of the stored signal segments is limited to just a few relevant exemplary signal segments, which considerably reduces the time expended on the assessment, particularly as regards the presence of health-critical respiratory states of the ventilated person. If a (wired or wireless) data transmission from the storage unit to an evaluation unit, for example arranged remotely from the breath analyzer, or to an expert user (e.g. physician) is provided or required for the assessment, the time expended on such data transmission is also advantageously reduced. Moreover, the storage unit can be equipped with a small memory, even for relatively protracted monitoring scenarios and breath analyses, which cuts down on the installation space for the implementation of the breath analyzer and also on the costs for its production.

It is to be understood that the curve analyzer and/or the comparator do not necessarily have to be physical functional units and instead can be implemented, for example, as software-based functional units which are correspondingly performed by the computing unit in order to make available their function as described herein.

According to an advantageous embodiment of the invention, the computing and storage unit is designed and configured to store, for each breath class, only a predetermined maximum number of signal segments in the storage unit. In other words, at the start of an analysis period, or once before the first start-up of the breath analyzer, a maximum number of signal segments to be stored per breath class can be predefined, for example a maximum of 3, 5 or 10 signal segments. It is preferable for a maximum of five signal segments per breath class to be stored by the breath analyzer, particularly preferably a maximum of three. Thus, on the one hand, there are a sufficient number of examples of relevant signal curves detected per breath class for an assessment, and, on the other hand, the storage requirement for such a small maximum number of signal segments to be stored is always very low.

Depending on the application, provision can be made that the maximum number of signal segments to be stored per breath class are the first assigned breathing patterns detected during an entire analysis duration or, for example, the last detected (most current) breathing patterns during the analysis duration.

For prioritization of breath classes, for example with respect to the severity of the health complication for the patient that is associated with the respective breath class, provision is made, in an advantageous embodiment of the invention, that the number of the plurality of signal segments to be stored can be fixed separately for at least two different breath classes. Thus, for a breath class that is particularly relevant to health, it is possible for example to predefine a higher maximum number of assigned breathing patterns that are detected during the analysis duration and are to be stored, whereas a smaller number of signal segments to be stored can be defined for less critical breath classes. Thus, optimal and efficient storage utilization is achievable with a still low storage requirement for storing all signal segments, although, for a precise assessment in certain breath classes, a higher number of stored breathing patterns compared to other breath classes may be necessary.

In a further advantageous embodiment of the invention, provision is made that the segment duration of the signal segment can be fixed on the basis of at least one predetermined signal curve criterion. The latter is preferably chosen from a group of criteria that includes at least one gradient and/or a gradient profile of the detected signal curve, an occurrence of at least one maximum and/or minimum of the signal curve and the like. Such dynamic, automatic fixing of the segment duration is considerably more flexible than a segment duration being firmly predefined once for example at the start of the analysis duration, and it permits automatic adaptation to the instantaneous respiratory situation of the person being ventilated. For example, the aforementioned criteria can be utilized to detect a start and an end of at least one complete breath and to determine this as a signal segment to be analyzed. Similarly, it is also possible for only a defined part of a signal curve of a breath to be contained in the defined signal segment. The gradient can be understood as the change of the signal curve over time, for example. From a gradient profile, it is possible, for example with a sign reversal (zero crossing of the gradient profile), to infer a rise of the signal in the signal curve followed by a fall of the signal, and vice versa. Thus, on the basis of the gradient profile, it is also possible to determine the contour of the actual signal curve.

Particularly preferably, the segment duration can be dimensioned such that the signal segment contains at least one complete breath, preferably 1 to a maximum of breaths, particularly preferably at least 3 to a maximum of 5 breaths.

In a further advantageous embodiment of the invention, provision is made that the stored signal segment is provided with a time stamp, for example the time of day and/or the date, of its determination, such that the occurrence of the detected breathing pattern can be easily established in a later assessment and accordingly taken into account in the evaluation.

Moreover, in another advantageous embodiment of the invention, provision is made that the comparator is designed and configured to assign the signal segment to the respective breath class by means of pattern recognition and/or by means of a comparison of the signal curve in the signal segment with a predetermined number of predefined reference signal curves stored beforehand in the storage unit and/or by means of a detected gradient and/or a gradient profile of the signal curve in the signal segment and/or by means of one or more detected maxima and/or minima of the signal curve in the signal segment. The gradient and the gradient profile permit the determination of a defined contour of the signal curve in the signal segment.

According to a further advantageous embodiment of the invention, the comparator is designed and configured to store a predetermined number of selected signal segments, assigned to the respective breath classes during the analysis duration (i.e. signal segments that have been detected or have occurred), as additional and newly added, adaptively learned reference signal curves in the storage unit and to take these into consideration when assigning subsequently detected signal segments to the breath classes. Thus, during the analysis duration, an automatic and dynamic adaptation of the breath analyzer to personalized individual breathing is permitted, in order to further increase the quality of the analysis result (classification rate and confidence).

According to a preferred further embodiment of the invention, the breath classes include at least the breath types inspiration, expiration, pause and cough. Preferably, the breath classes additionally comprise breath types which represent an inspiratory flow limitation and/or an expiratory flow limitation and/or an intrinsic PEEP (positive end-expiratory pressure) and/or breath asynchrony types such as ineffective breathing effort (e.g. ineffective inspiration effort, lack of inspiration trigger) and/or a double breathing effort (e.g. further inspiration effort at the start of an expiration as a result of too short an inspiration time, designated herein as double triggering). The asynchrony types represent in particular an asynchrony between the breathing of the ventilated person and the ventilation pressure (predefined for example by a ventilator) of the respiratory gas. Events such as inspiratory flow limitation, lack of inspiration trigger, cough, expiratory flow limitation, intrinsic PEEP and the like can be detected by the breath analyzer for example by means of a comparison of the signal curve in the signal segment with a predetermined number of predefined and/or adaptively learned reference signal curves stored beforehand in the storage unit, and/or by means of a detected gradient and/or a gradient profile of the signal curve in the signal segment, and/or by means of one or more detected maxima and/or minima of the signal curve in the signal segment.

According to a further advantageous embodiment, the comparator is designed and configured to receive additional information concerning the breath type, such as spontaneous or mandatory breathing, and/or concerning a speed of rotation of a ventilation fan delivering the respiratory gas to the person, and/or concerning a leakage loss of the respiratory gas delivered to the person, and to take this additional information into account when assigning the signal segment to the breath classes. The additional information can be used, for example, for more precise assignment of the signal curve in the signal segment to the correct breath class by the comparator on the basis of corresponding pre-processing (e.g. standardization of the signal curve).

According to the invention, internal and/or optional external or adaptable sensors can be used to deliver the information concerning the breathing activity or respiratory gas values or parameters. Particularly for the identification of respiratory efforts or of the breathing activity, use can be made of acceleration sensors on the upper body, strain or tension sensors in a belt around the upper body, EMG sensors on the respiratory muscles or the diaphragm, a pressure sensor in the airways, impedance sensors in a belt around the upper body, measurement of chest impedance via electrodes, measurement of respiratory sounds, measurement of SpO2 or transcutaneous CO2 or CO2 in the exhaled air, measurement of pulse or ECG, each of these alone or in combination. The signal curves of these sensors can be evaluated according to the principles of this invention and can be used alone in combination in order to improve the pressure and/or flow and/or volume characteristics of the ventilator, such that fewer or less serious breathing events occur.

It should be noted that the signal curve in the signal segment can be evaluated on the basis of a time profile of the signal, for example of the respiratory flow over time. Alternatively or in addition, the evaluation of the signal, for example of the respiratory flow or tidal volume, can also be effected via the ventilation pressure (so-called P/V diagram).

A further aspect of the invention concerns a ventilator for ventilating a person with a respiratory gas, having a sensor unit for determining a ventilation pressure and/or a respiratory flow and/or a tidal volume of the respiratory gas delivered to the person. Moreover, the ventilator according to the invention has a breath analyzer according to one of the preceding embodiments, wherein the sensor unit is coupled in a data-transmitting manner to the computing and storage unit of the breath analyzer and is configured to generate a signal corresponding to the determined ventilation pressure and/or to the determined respiratory flow and/or to the determined tidal volume of the respiratory gas and to deliver this signal to the computing and storage unit.

With respect to ventilator-related definitions of terms, and the effects and advantages of those features, reference is made in full to the above explanations of corresponding definitions, effects and advantages relating to the breath analyzer according to the invention. Disclosures herein concerning the breath analyzer according to the invention may be used accordingly for definition of the ventilator according to the invention, unless expressly excluded herein. Also, disclosures herein concerning the ventilator according to the invention may be used accordingly for definition of the breath analyzer according to the invention, also unless expressly excluded herein. In this respect, repetition of explanations of features of identical meaning and the effects and advantages thereof in respect of the breath analyzer according to the invention disclosed herein and the ventilator according to the invention disclosed herein are substantially omitted below in favor of a more concise description.

In an advantageous embodiment of the invention, provision is made that the ventilator has at least one data transmission interface which is designed and configured to transmit to a data receiver, or a data receiver unit, the content, stored in the storage unit, of the frequency counter of each breath class and/or the at least one signal segment, stored in the storage unit, of each assigned breath class (i.e. each breath class occurring during the analysis duration). The data transmission here can be by wire or wireless. Data transmission interfaces can be, for example, an electronic data transmission bus, a network interface (e.g. LAN), a data transmission modem, a USB interface, a radio transmission interface, e.g. infrared, Bluetooth, WIFI, GSM/LTE and the like, or also an exchangeable storage medium, e.g. a memory card (Flash), a USB stick/hard disk and the like. The data receiver or the data receiver unit can be, for example, an external (remote) data processor with an evaluation unit (e.g. evaluation software), an expert user (e.g. physician), a display device (e.g. display, monitor) and the like. The data receiver unit can thus permit assessment of the analysis result at a later time, particularly in the case where the ventilator has no internal evaluation unit. However, the ventilator can alternatively or additionally have an internal evaluation unit.

According to a further advantageous embodiment of the invention, the ventilator has a further sensor unit designed to detect a speed of rotation of a ventilation fan and/or a leakage loss of the respiratory gas during the ventilation of the person and/or a breath type such as spontaneous breathing or mandatory breathing, and to deliver this to the breath analyzer.

According to another advantageous development, the ventilator has an evaluation unit which is designed and configured to evaluate the analysis result of the breath analyzer in terms of health-critical complications of the ventilated person and to store it in the storage unit and/or display it on a display device and/or transmit it to an external data receiver unit. For this purpose, the data transmission can be effected in particular via the aforementioned data transmission interface. The data receiver unit is to be understood in particular as a monitoring unit, a monitor in a hospital or nursing home, and, in the case of ventilation at home, a telemonitoring server. If the frequency and/or the severity of an established complication exceeds a fixed limit value, the ventilator can likewise be designed to output an alarm, for example on the display device, and/or to send an alarm to the data receiver unit.

According to a further advantageous embodiment of the invention, provision is made that the breath class ineffective breathing effort is detected by the fact that the respiratory flow during the expiration phase is analyzed, and the respiratory flow during the expiration phase has at least intermittently a sign reversal.

According to a further advantageous embodiment of the invention, provision is made that the breath class ineffective breathing effort is detected by analyzing whether the exhalation flow within a first time window at the start of expiration exceeds a defined threshold (e.g. in 1/min) and thereafter decreases within a second time window until it falls below a certain threshold, or there is even briefly a positive, i.e. inspiratory, respiratory flow or at least the derivation of the respiratory flow points to a decrease of the expiratory flow, wherein a check is then made as to whether the exhalation flow increases again within a third time window, i.e. there is once again a stronger exhalation flow, or at least the derivation of the respiratory flow points to a renewed increase of the expiratory flow, even before the next inspiration is detected.

According to a further advantageous embodiment of the invention, provision is made that the breath class ineffective breathing effort is detected by virtue of the fact that the ineffective inspiration effort is detected by a pattern recognition which compares the curve of the respiratory flow with previously stored test patterns that represent ineffective inspiration efforts.

According to a further advantageous embodiment of the invention, provision is made that the breath class ineffective breathing effort is detected by virtue of the fact that the breath class double triggering is detected by comparing the exhalation time with a multiplicity of preceding (typical) exhalation times or with an average exhalation time or a predefined exhalation time.

According to a further advantageous embodiment of the invention, provision is made that the breath class ineffective breathing effort is detected by virtue of the fact that the breath class double triggering is detected by comparing the measured flow with a theoretical respiratory flow, wherein the measured flow remains high in relation to the theoretical respiratory flow after the switch to expiratory ventilation pressure.

According to a further advantageous embodiment of the invention, provision is made that the detection of the breath class intrinsic PEEP is effected on the basis of stored exemplary curve profiles of flow or volume which are representative of an intrinsic PEEP, wherein current curve profiles are for this purpose compared with the stored curve profiles.

According to a further advantageous embodiment of the invention, provision is made that the detection of the breath class intrinsic PEEP is effected by an evaluation of the temporal flow or volume distribution within the expiration, wherein at the start of the expiration a high exhalation flow is detected which then decreases and, in the further course of the expiration, transitions into a low exhalation flow.

According to a further advantageous embodiment of the invention, provision is made that the detection of the breath class intrinsic PEEP is effected by detection of an inspiration effort of the patient and by evaluation of the exhalation flow in the time range of the inspiration effort, wherein the remaining expiratory flow in the time range of initiation of the next inspiration phase is representative of the extent of the intrinsic PEEP.

According to a further advantageous embodiment of the invention, provision is made that the detection of the breath class cough is effected by pattern recognition of the expiration curve of flow or volume on the basis of stored curves which are representative of coughs, wherein current curves are for this purpose compared with the stored curves.

According to a further advantageous embodiment of the invention, provision is made that the detection of the breath class cough is effected by comparing the curve of the current exhalation flow, the peak exhalation flow or peak exhalation volume with the typical preceding exhalation flows, peak exhalation flows or peak exhalation volumes of the patient for detection of a forced exhalation that points to a cough, wherein a cough is detected when the current breath reaches more than about 70% or more than about 140% or more than about 200% of the typical breaths.

According to a further aspect of the invention, a method for analyzing breathing events of a person ventilated with a respiratory gas is made available, in which method a signal corresponding to a ventilation pressure and/or a respiratory flow and/or a tidal volume of the respiratory gas delivered to the person is generated by means of a sensor unit and, during a predetermined analysis duration, a time curve of the signal is determined. Thereafter, in particular directly after its determination, a signal segment is determined from the determined signal curve, which signal segment, on the basis of a predefined segment duration or a segment duration detected from the signal curve, is set shorter than the analysis duration. The determined signal segment is then assigned to one of several breath classes, wherein in each case a frequency of occurrence, of the breath class assigned during the analysis duration, is stored in a frequency counter provided for each breath class, and at least one of the signal segments determined during the analysis duration, but fewer than the frequency of occurrence detected in the frequency counter, is stored for each assigned breath class.

In a further aspect of the invention, the ventilator can also react intelligently or auto-adaptively, in order to minimize the occurrence of at least some breathing events. The ventilator is configured and designed to identify individual breathing events and to change the ventilation pressure and/or the flow and/or the volume of the respiratory gas, separately for inspiration and expiration, according to the breathing event or the frequency or significance of the breathing event, in such a way that the breathing event or the frequency or significance of the breathing event is attenuated or decreases. For example, the trigger sensitivity can be adapted for the detection of breathing efforts of the patient in the case of detected asynchronies, namely when breathing efforts of the patient are absent or take place at an unexpected time or at a time outside an expectation window. The expiratory pressure can be increased or reduced: it can be increased, in particular at the start of the expiration, and then reduced, or it can be increased at the end of the expiration. The pressure curve when switching from the inspiratory pressure to the expiratory pressure (splinting of the airways in expiration) can be adapted to minimize the intrinsic PEEP.

In a further aspect of the invention, upon detection of an inspiratory flow limitation and/or an expiratory flow limitation and/or an intrinsic PEEP and/or an ineffective breathing effort and/or a double breathing effort (double triggering), the ventilator can generate at least one message via the data transmission interface and/or on the display or store it in data and/or at least one setting of the ventilation is changed, for example chosen from IPAP and/or EPAP and/or inspiration time and/or expiration time and/or trigger sensitivity.

It is again noted that, with respect to method-related definitions of terms, and the effects and advantages of those features, reference is made in full to the above explanations of corresponding definitions, effects and advantages relating to the devices(s) according to the invention. Accordingly, disclosures herein concerning the device(s) according to the invention may be used accordingly for definition of the method according to the invention, and disclosures herein concerning the method according to the invention may be used accordingly for definition of the device(s) according to the invention. Repetition of explanations of features of identical meaning and the effects and advantages thereof is thus substantially omitted.

BRIEF DESCRIPTION OF THE DRAWINGS

Further features and advantages of the invention will become clear from the following description of non-limiting illustrative embodiments of the invention, which are explained in more detail below with reference to the drawings. In the schematic drawings:

FIGS. 4A, 4B and 4C show examples of signal curves of a signal, of a first breath class, corresponding to a ventilation pressure, a respiratory flow and tidal volume.

Parts that are equivalent in terms of their function are always provided with the same reference signs in the different figures, and therefore these parts are also generally described just once.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
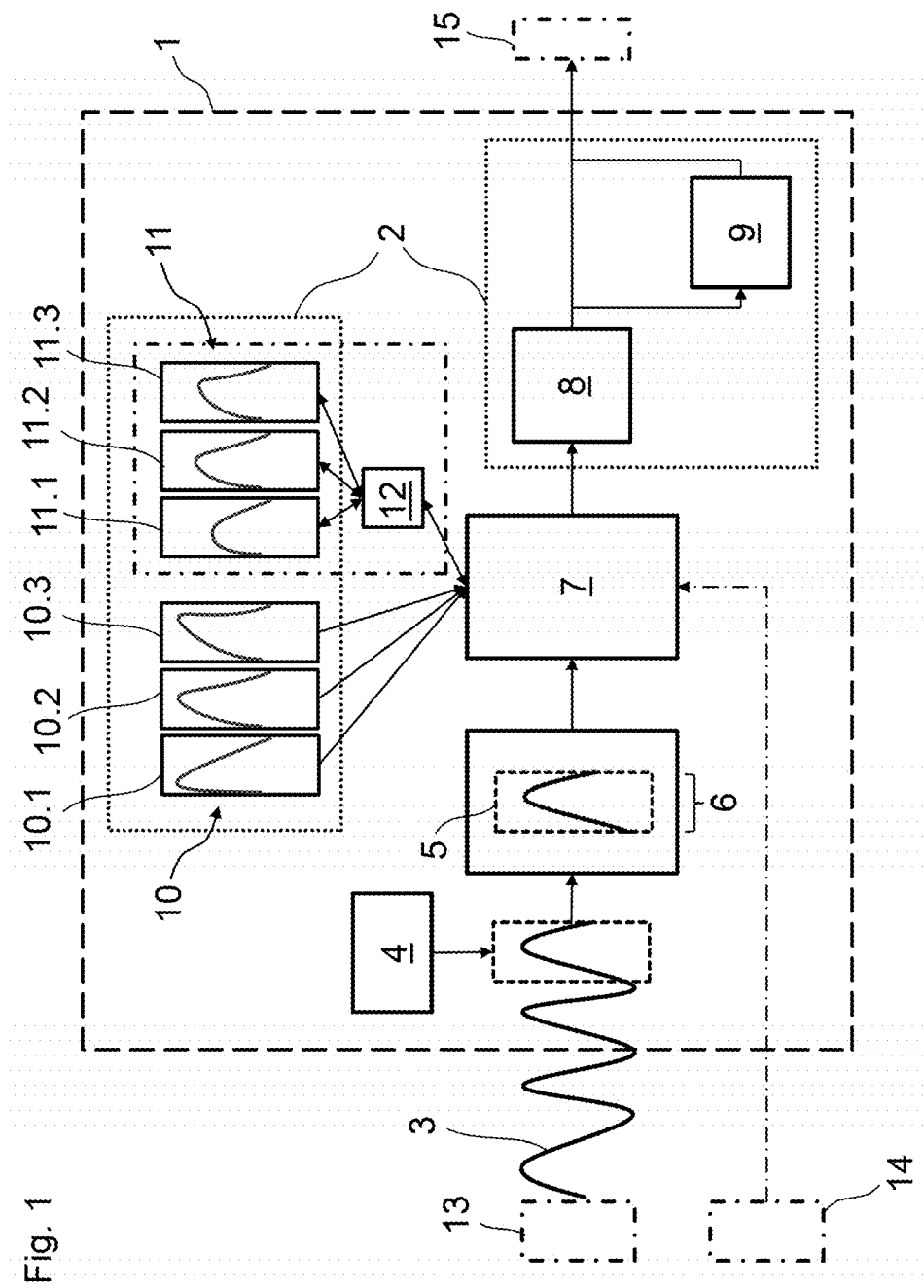
FIG. 1 shows a functional diagram of an illustrative embodiment of a breath analyzer according to the invention.

FIG. 1 shows schematically a functional diagram of an illustrative embodiment of a breath analyzer 1 according to the invention for the detection of breathing events of a person (not shown) ventilated with a respiratory gas. The breath analyzer 1 shown has an electronic (in the present instance a processor-based) computing and storage unit, of which only the storage unit 2 is shown schematically in FIG. 1 with a dotted border, which is designed and configured to receive a signal 3 corresponding to a ventilation pressure and/or a respiratory flow and/or a tidal volume of the respiratory gas delivered to the person and, during a predetermined analysis duration, to detect a curve of the signal 3 by means of a curve analyzer 4. The computing and storage unit 2 of the breath analyzer 1 shown is further designed and configured to determine from the signal curve a signal segment 5 which is fixed here on the basis of a segment duration 6 which is detected from the signal curve and which is substantially shorter than the analysis duration and can for example comprise one or also several complete breaths (e.g. 1-3 breaths), and to assign the determined signal segment 5 by means of a comparator 7 to one of several predefined breath classes, and in each case to store a frequency of occurrence, of the breath class assigned during the analysis duration, in a frequency counter 8 provided for each breath class in the storage unit 2, and to store at least one of the signal segments 5 determined during the analysis duration, but fewer than the frequency of occurrence detected overall in the frequency counter 8, for each assigned breath class in the storage unit 2, in FIG. 1 in a storage region 9 of the storage unit 2 for signal segments.

It will also be seen from FIG. 1 that the breath analyzer 1 has a plurality of predefined reference signal curves 10, of which three are shown by way of example in FIG. 1, and which are stored in the storage unit 2. It will be understood that a plurality of reference signal curves 10.1 to 10.n can be stored for each breath class. The predefined reference signal curves 10.1 to 10.n can be used by the comparator 7 to compare the instantaneously detected signal segment 5, so as to assign the signal segment 5 to a breath class representing the reference signal curves.

In the breath analyzer 1 shown in FIG. 1, it is further indicated that optionally (dot-and-dash border), during the operation or the analysis duration, adaptively learned further reference signal curves 11 per breath class, of which three adaptively learned reference signal curves 11.1, 11.2, 11.3 of a breath class are shown by way of example in FIG. 1, are stored in the storage unit 2. It will be understood that the number of predefined reference signal curves 10 and also of adaptively learned reference signal curves 11 per breath class can be predefined according to the intended use of the breath analyzer 1. For the adaptive learning of the reference signal curves 11, the breath analyzer 1 optionally has an adaptive learning unit 12 which, in order to learn and expand the adaptively learned reference signal curves 11, on the one hand receives signal segment data from the comparator 7 and on the other hand provides the comparator 7 with already learned reference signal curves 11 for the assigning of the signal segments 5 to the respective breath classes.

It is further indicated in FIG. 1 that the signal 3 is generated by a sensor unit 13 external to the analyzer. Moreover, further information, for example concerning the breath type, in particular spontaneous or mandatory breathing, and/or concerning a speed of rotation of a ventilation fan (not shown) delivering the respiratory gas to the person, and/or concerning a leakage loss of the respiratory gas delivered to the person, can selectively be fed to the breath analyzer 1 via a further, optional second sensor unit 14.

Moreover, at least the analysis data stored in the storage unit 2 and obtained during the analysis duration, here in particular the content of the respective frequency counter 8 per breath class and/or the content of the storage region 9 which stores the detected signal segments per breath class during the analysis duration, can be transmitted via an optional data transmission interface 15 to a data receiver (not shown in FIG. 1).

Figure 2:
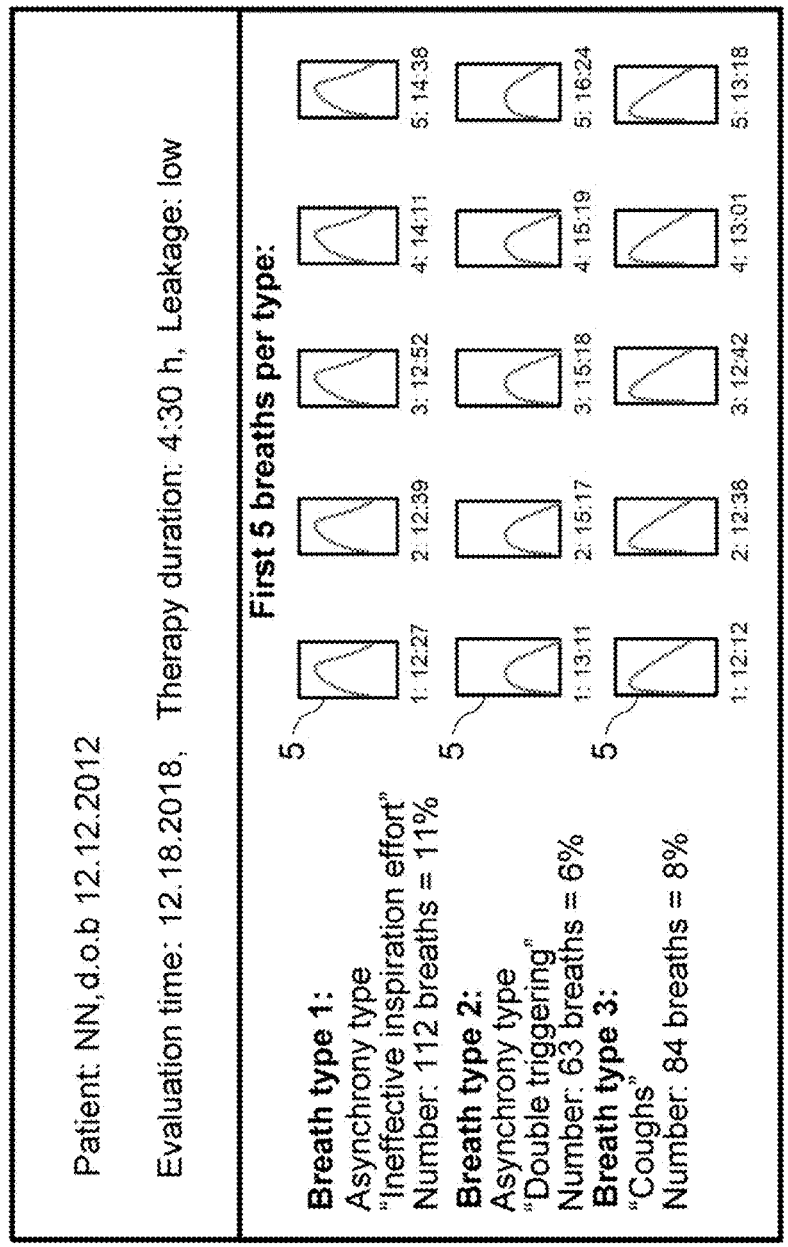
FIG. 2 shows an overview of analysis results, obtained by means of the breath analyzer of FIG. 1, for a short time period.

FIG. 2 shows an overview of analysis results, for example obtained by means of the breath analyzer 1 from FIG. 1, for a relatively short total analysis duration, here 4.5 hours. The overview shows generally a time stamp, here a date of the analysis performed, and additional leakage information (here "low") during the analysis duration. The illustrated overview additionally shows three different breath classes, here designated as breath or asynchrony type 1 ("Ineffective inspiration effort"), asynchrony type 2 ("Double inspiration effort/double triggering") and breath type ("Coughs"), wherein the five first (stored) signal segments 5 detected during the analysis duration are shown by way of example for each breath class. Each signal segment 5 is additionally indicated with a time stamp, here the time of day when the respective signal segment 5 was determined. For each of the three breath classes indicated, the overall absolute frequency (stored in the frequency counter 8 of the breath analyzer 1 from FIG. 1) determined for the respectively detected breath class (here types 1 to 3) during the analysis duration is likewise indicated, and also the relative frequency in percent relative to the breaths detected overall during the analysis duration.

Figure 3:
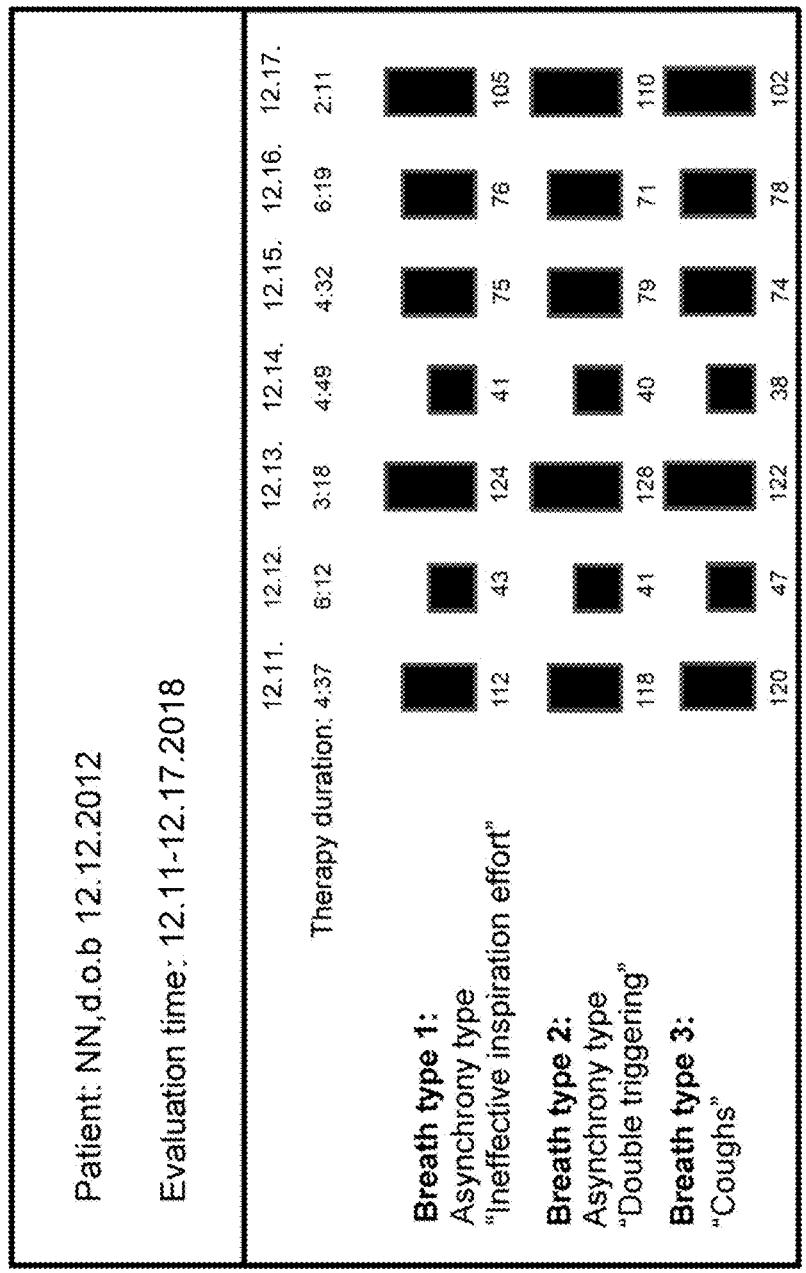
FIG. 3 shows a further overview of analysis results, obtained by means of the breath analyzer of FIG. 1, for a long time period.

FIG. 3 shows a further overview of analysis results, obtained by means of the breath analyzer 1 from FIG. 1, for a long analysis period, here seven days, wherein on each day an analysis was carried out with analysis periods of different lengths, as can be seen from FIG. 3 on the basis of the respective time stamp (date and duration). The analysis results are in each case shown for each breath class as in FIG. 2, wherein in the overview of FIG. 3 the absolute frequencies of the detected breath classes during the respective analysis duration are indicated per day.

FIGS. 4A, 4B, 4C, 5A, 5B, 6A, 6B, 7A and 7B each show examples of signal curves of a signal of a first, second, third and fourth breath class, said signal corresponding to a ventilation pressure, a respiratory flow and a tidal volume. The respective views (a) show the signal curves for the ventilation pressure, respiratory flow, tidal volume and a breath phase (inspiration phase 16 and expiration phase 17) of an uneventful signal curve.

For the breath class "Ineffective inspiration effort" (type 1) indicated in FIGS. 2 and 3, that is to say missed breaths of a person ventilated with a ventilator during the expiration phase 17 of the ventilator, FIG. 4B shows the typical signal curve at the locations 18 of the respiratory flow. "Ineffective inspiration efforts" 18 are ineffective breathing efforts by the patient which correspond to an attempt at inspiration but are in most cases subliminal and do not therefore initiate a switch to the inspiration phase (by the ventilator).

"Ineffective inspiration efforts" 18 are detected by analyzing the respiratory flow during the expiration phase 17. The respiratory flow during the expiration phase 17 would normally fall permanently below the zero line, i.e. the sensor registers a (negative) flow directed in the direction of the ventilator. "Ineffective inspiration efforts" have a curve in which at first (for 0.1 to 4 seconds or for 10-90% of the inspiratory flow) a negative flow is recorded. A sign reversal of the flow is then detected, and the flow approaches the zero line or is temporarily positive. Thereafter, the flow can reverse again and once more become negative and fall below the zero line. "Ineffective inspiration effort" can generally be detected by the fact that, in the respiratory flow during the expiration phase 17, a sign reversal of the flow is detected at least temporarily and/or the flow again exceeds the zero line at least temporarily.

In one embodiment, this can be determined by checking whether the exhalation flow within a first time window, for example within a fixed time or a portion of the typical expiration duration, exceeds a defined threshold (e.g. in 1/min) at the start of expiration and thereafter decreases within a second time window until it falls below a certain threshold (e.g. in 1/min) or there is even briefly a positive, i.e. inspiratory, respiratory flow, or at least the derivation of the respiratory flow points to a decrease of the threshold of the expiratory flow.

A check is then made to ascertain whether the exhalation flow within a third time window increases again, i.e. there is once again a stronger exhalation flow, or at least the derivation of the respiratory flow points to a renewed increase of the threshold of the expiratory flow, even before the next inspiration is detected.

The time windows are preferably chosen here in a range of between about 0.1 and about 3 seconds, or in each case between about 10 and about 90% of the typical exhalation duration.

Alternatively, the ineffective inspiration effort can also be detected by a pattern recognition which analyzes the curve of the respiratory flow and which has learnt beforehand, on the basis of test patterns, how to detect ineffective inspiration efforts.

Figure 4C:
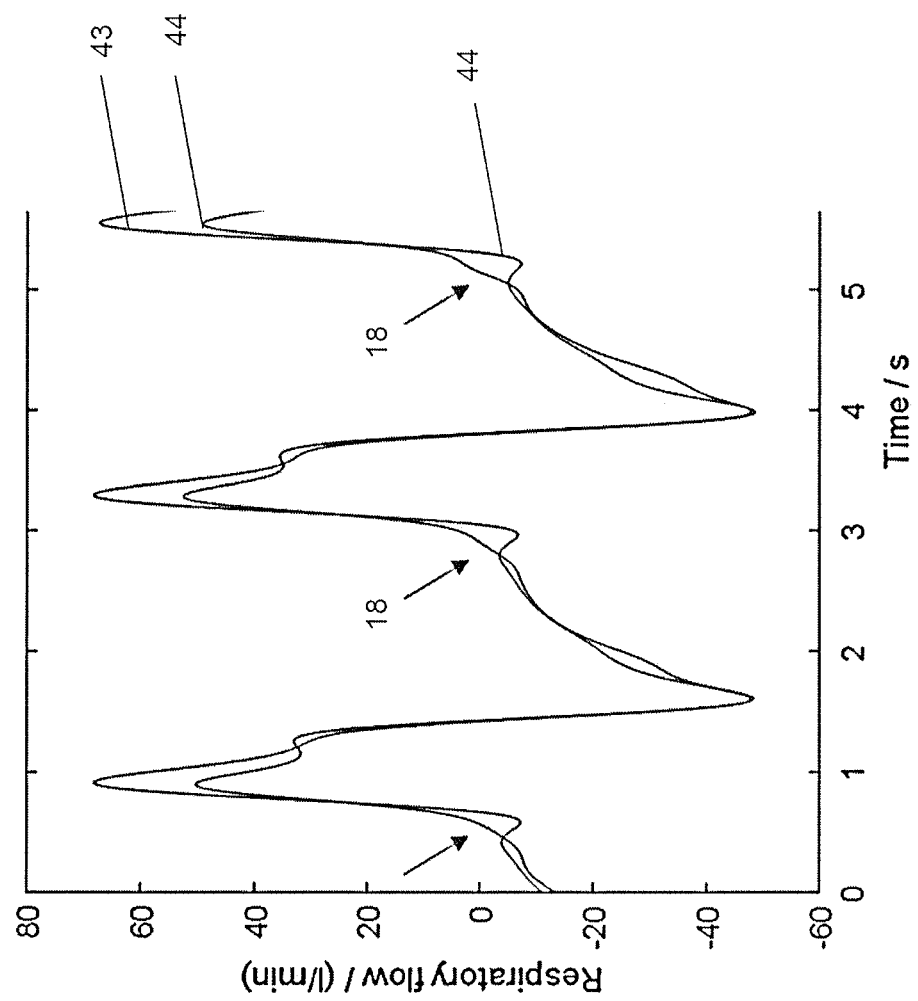

Alternatively, according to FIG. 4C, an ideal or passive respiratory flow curve 43 can be determined which would occur in purely passive ventilation of the patient, i.e. without spontaneous breathing exertion, on the basis of the measured pressure curve, if one were to apply this pressure curve to the lungs of the patient. The lung parameters of the patient, such as compliance and resistance of different lung regions, are determined in advance or estimated by the ventilator. The passive respiratory flow curve is then compared with the actually measured respiratory flow curve 44.

If the actually measured respiratory flow curve deviates from the determined passive respiratory flow curve, the difference can be used to estimate, inter alia, the breathing exertion of the patient. If, within one expiration, a transient inspiration effort 18 is detected that exceeds a previously defined threshold, it is likewise possible to infer an ineffective inspiration effort. If an inspiration effort 18 is detected that successfully initiates an inspiration trigger of the ventilator, i.e. an effective inspiration effort, then the reaction time of the inhalation trigger can be determined as a time difference between inspiration effort 18 and the increase of the therapy pressure to the inspiratory therapy pressure.

FIG. 4C shows the ideal or passive respiratory flow curve 43 without breathing exertion and airway obstructions, which arises when the curve of the therapy pressure is applied to a lung model with at least one compliance and resistance, and the actual respiratory flow curve 44. The inspiration efforts 18 are detected by the fact that the measured respiratory flow increases even though the therapy pressure and therefore also the theoretical passive respiratory flow do not yet increase. The time difference between both flow curves is determined as the trigger delay time. If the trigger delay time is high, for example greater than 200 ms, then the respiratory work of the patient increases and there is a danger of ineffective inspiration efforts 18 occurring. If the trigger delay time is very low, for example less than 50 ms, there is a danger that breaths are initiated even without inspiration effort 18 of the patient, so-called auto-triggering of the ventilator. Both cases, too high a trigger delay time and too low a trigger delay time, can adversely affect the subjective and objective outcome of the ventilation.

An "ineffective inspiration effort" and preferably also a report on the trigger delay time are transmitted telemedically to the physician and/or displayed or stored in the appliance. In addition, the appliance or an external display device generates a therapy recommendation or performs the latter automatically. Here, the trigger sensitivity is preferably changed, or the expiration duration is shortened or the inspiratory therapy pressure is changed in order, through a change of the tidal volume, to change the respiratory drive or the spontaneous respiratory rate, such that inspiration efforts 18 occur either earlier (higher inspiration pressure) or later (lower inspiration pressure). Alternatively, the expiratory therapy pressure can also be increased in the case of a prolonged trigger delay time or ineffective inspiration efforts 18. This is advantageous particularly if the patient, as a result of air trapped in the lung, has an elevated lung pressure at the end of the expiration (intrinsic PEEP) which is higher than the expiratory therapy pressure of the ventilator, such that the pressure difference iPEEP minus PEEP of the ventilator has to be overcome by the patient in order to initiate a trigger of the ventilator. For example, in such a case, the expiratory therapy pressure can be at least temporarily higher than the inspiratory pressure.

Preferred rules for an automatic selection of a more sensitive trigger, for example by lowering the flow threshold for initiation of the trigger, or increasing the inspiratory therapy pressure to prolong the exhalation phases without renewed inspiratory drive, or increasing the expiratory therapy pressure to reduce the difference between iPEEP and PEEP of the ventilator which has to be overcome to initiate an inspiration trigger:

- A detected ineffective inspiration effort
- The exceeding of a defined number of ineffective inspiration efforts within a time window, for example more than 2 ineffective inspiration efforts in 2 minutes
- An increased trigger delay time
- An increased average trigger delay time within a time window, for example 2 min
- The exceeding of a defined number of breaths with an increased trigger delay time within a time window
- The sum of the number of ineffective inspiration efforts and the number of breaths with an increased trigger delay time exceeds a defined number within a time window
- The number of ineffective inspiration efforts per time window is greater than the number of breaths with a very short trigger delay time within a time window
- The sum of the number of ineffective inspiration efforts and the number of breaths with an increased trigger delay time is greater than the number of breaths with a very short trigger delay time within a time window A more sensitive trigger is then predefined, for example, by lowering the flow threshold that is needed to initiate the trigger, or increasing the inspiratory therapy pressure to prolong the exhalation phases without renewed inspiratory drive, or increasing the expiratory therapy pressure to reduce the difference between iPEEP and PEEP of the ventilator which has to be overcome to initiate an inspiration trigger.

For lowering the trigger sensitivity that is predefined, for example by raising the flow threshold to initiate the trigger, or lowering the inspiratory therapy pressure, or lowering the expiratory airway pressure, the corresponding inverse rules apply.

Figure 5A:
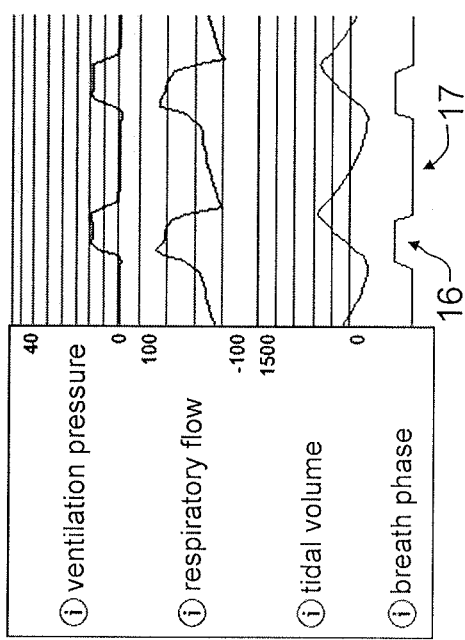
FIGS. 5A and 5B show examples of signal curves of a signal, of a second breath class, corresponding to a ventilation pressure, a respiratory flow and tidal volume.
Figure 5B:
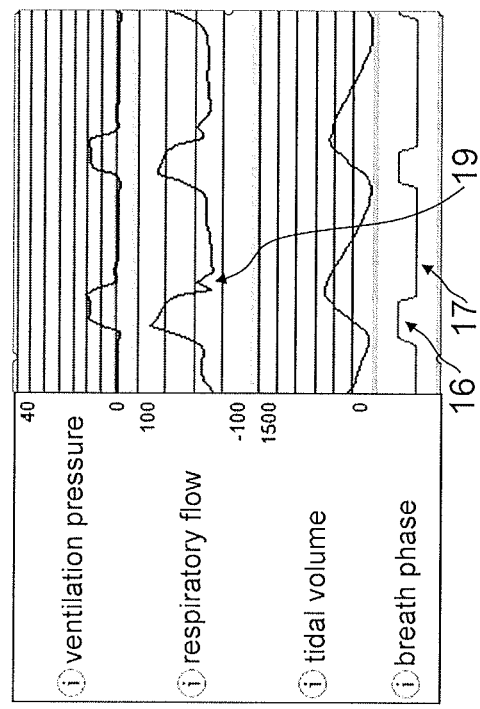

FIG. 5B shows the typical signal curve, at the location of the respiratory flow, for the breath class "Double triggering" (type 2) indicated in FIGS. 2 and 3, that is to say further inspiration effort, of the person ventilated with a ventilator, at the start of the expiration phase 17 of the ventilator.

Such double triggering is detected for example via a greatly shortened exhalation time compared to the typical, for example average, or predefined exhalation time, either once or at x breaths within a time window. Such double triggering is also detected for example via the measured flow which, after a switch to expiratory ventilation pressure, remains elevated in relation to the theoretical, passive respiratory flow.

When such double triggering is detected, the treatment provider receives notification by telemonitoring or on the display or in the form of stored data.

Alternatively or in addition, when such double triggering is detected, there is an automatic reduction of the sensitivity of the expiration trigger, i.e. a later initiation of the expiration trigger, and/or an automatic lengthening of a predefined inspiration time, and/or an automatic application of a trigger block time within which, after switching to the expiratory ventilation pressure, no renewed inspiration trigger may be initiated, and/or an increase of the inspiratory ventilation pressure, such that the lungs fill more quickly with air and the inspiration time of the patient becomes shorter.

Figure 6A:
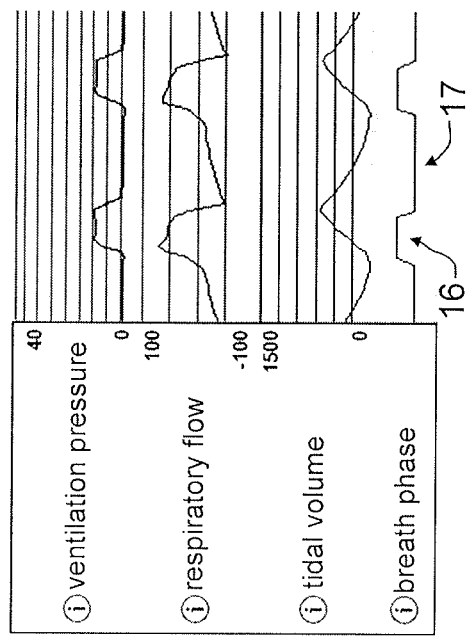
FIGS. 6A and 6B show examples of third signal curves of a signal, of a third breath class, corresponding to a ventilation pressure, a respiratory flow and tidal volume.
Figure 6B:
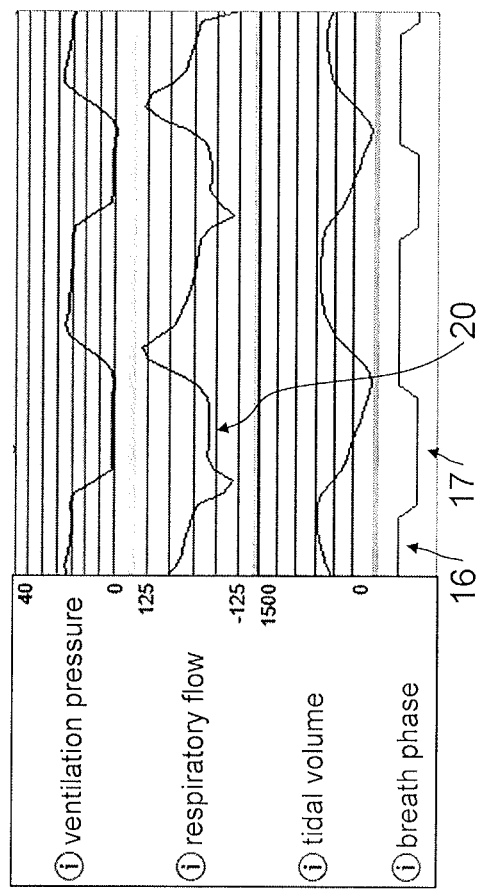

FIG. 6B shows the typical signal curve at the location of the respiratory flow for a breath class "Intrinsic PEEP", that is to say during the expiration phase 17 the air volume inhaled by a person ventilated by a ventilator cannot be completely exhaled.

The intrinsic PEEP 20 is detected for example on the basis of stored exemplary curve profiles of flow or volume that are representative of an intrinsic PEEP 20. Current curve profiles are for this purpose compared with the stored curve profiles.

Alternatively, the intrinsic PEEP 20 is also detected by an evaluation of the temporal flow or volume distribution within the expiration. It is typical of an intrinsic PEEP 20 if, at the start of the expiration, a high exhalation flow is detected, which then abruptly decreases and, in the further course of the expiration, transitions into a very low exhalation flow (for example lower than a threshold value).

Alternatively, the intrinsic PEEP 20 is detected by comparison/correlation of the curve of the exhalation flow with stored comparison curves for exhalation flows at normal expiration and at expiration with increased resistance, which can lead to an iPEEP.

The intrinsic PEEP 20 is also detected by comparing the actual exhalation flow with the theoretical, passive exhalation flow based on the curve of the ventilation pressure and on the patient's lung parameters defined beforehand or estimated during runtime. If the exhalation flow is lower, i.e. the lungs empty more slowly than would be the case in ideal passive exhalation, an additional resistance in the exhalation must impede the respiratory flow. There must therefore be an obstruction of the airways, a so-called expiratory flow limitation, which often leads to iPEEP.

A detection of an inspiration effort 18 by the patient and evaluation of the exhalation flow at the moment of the inspiration effort 18 or at the moment of use of the background frequency of the ventilator is also utilized to detect the intrinsic PEEP 20. The greater the remaining expiratory flow at the moment of the initiation of the next inspiration, the greater the intrinsic PEEP or the air quantity trapped in the lungs.

According to the invention, provision is also made for counting of breaths with a high degree of expiratory flow limitation, in a defined period (or with suspected iPEEP) of between several minutes and one day, in order to detect an intrinsic PEEP 20.

Moreover, formation of an average degree of expiratory flow limitation/iPEEP in a defined period of between several minutes and one day can take place, in order thereby to detect an intrinsic PEEP 20.

When an intrinsic PEEP 20 is detected, the treatment provider receives notification by telemonitoring and/or on the display or in stored data.

Particularly in the case of a rapid change, i.e. over some hours to a few days, with a pronounced increase in the expiratory flow limitation, a high-priority warning (message) is advantageous, since either the quality of the ventilation or the condition of the patient has deteriorated.

When an intrinsic PEEP 20 is detected, there is alternatively an automatic adaptation of the pressure ramp from IPAP to EPAP, i.e. of the transition from the inspiratory ventilation pressure to the expiratory ventilation pressure. If this ramp is flatter, or is flatter in a second part of the expiration, or if the pressure in a second part of the expiration is raised again, then the lower airways are prevented from collapsing, and the expiratory flow limitation becomes weaker, hence also the iPEEP.

When an intrinsic PEEP 20 is detected, the expiratory pressure level is alternatively increased to splint the lower airways and to reduce the respiratory work for initiating the inspiratory trigger. The expiratory pressure can then temporarily lie above the inspiratory pressure.

Figure 7A:
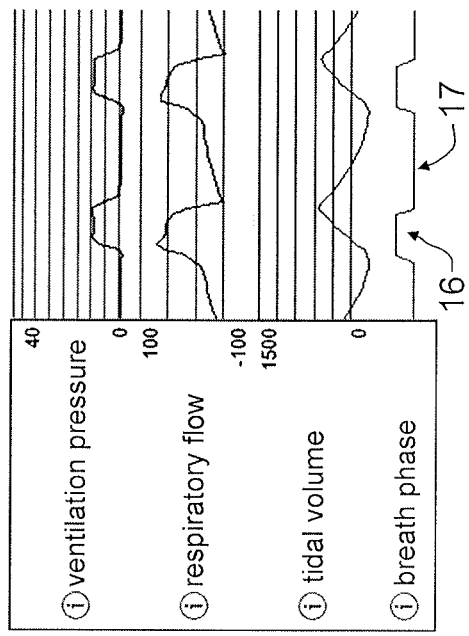
FIGS. 7A and 7B show examples of fourth signal curves of a signal, of a fourth breath class, corresponding to a ventilation pressure, a respiratory flow and tidal volume.
Figure 7B:
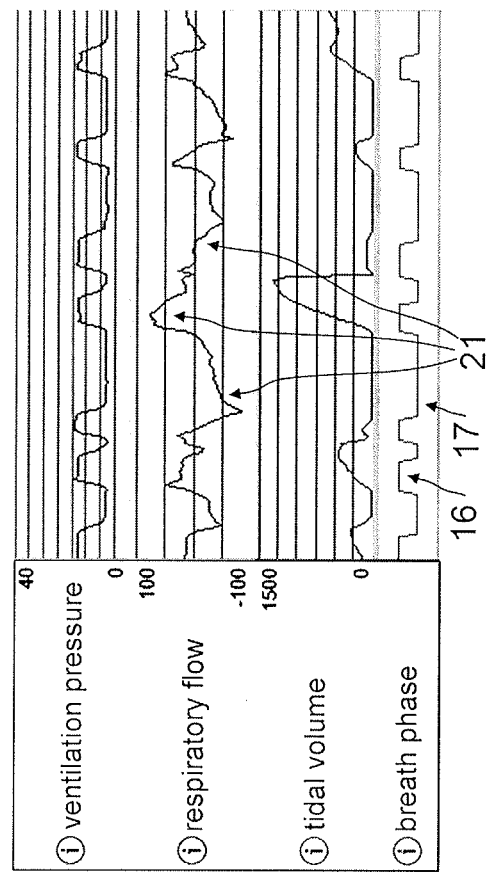

FIG. 7B shows the typical signal curve at the location of the respiratory flow for the breath class "Coughs" (type 3) indicated in FIGS. 2 and 3, that is to say increased, forced and prolonged inhalation and exhalation of the person ventilated by a ventilator.

Coughs 21 are detected for example via a pattern recognition of the expiration curve on the basis of exemplary curves that are stored. Current curve profiles are for this purpose compared with the stored curve profiles.

Coughs 21 are also detected by a comparison/correlation of the curve of the exhalation flow, of the peak exhalation flow or volume, with the typical, for example average, exhalation flows, peak exhalation flows or volumes of the patient, in order to detect a forced exhalation, which points to a cough. A cough is suspected, for example, if the current breath reaches over 120% or 150% or 200% of the typical breaths.

Coughs 21 are alternatively detected by additional detection of whether an increased exhalation is also preceded by an increased inhalation, measured on the volume or flow or peak flow, which corroborates the suspicion of coughing.

Coughs 21 are additionally detected by a comparison of the actual exhalation flow with the theoretical, passive exhalation flow based on the curve of the ventilation pressure and on the patient's lung parameters defined beforehand or estimated during runtime. If the exhalation flow is greater, i.e. if the lungs empty more quickly than would be the case in ideal passive exhalation, forced exhalation must be present. The threshold of the forced exhalation can be determined, for example, via the volume difference between the actual and the ideal passive exhalation or from the difference of the two flow curves. If the difference of the volume or of the flow exceeds a certain value, then a cough is detected.

Coughs 21 are also detected by a comparison of the derivation of the respiratory flow according to one of the stated criteria.

When coughs 21 are detected, the treatment provider receives notification by telemonitoring and/or on the display or in stored data. Particularly in the case of a rapid change, i.e. over some hours to a few days, with a pronounced increase in the expiratory flow limitation, a high-priority warning (message) is advantageous, since either the quality of the ventilation or the condition of the patient has deteriorated.

Particularly in the case of a rapid change, i.e. over some hours to a few days, with a pronounced increase in the coughing frequency, a high-priority warning is advantageous, since either the quality of the ventilation or the condition of the patient has deteriorated.

Figure 8:
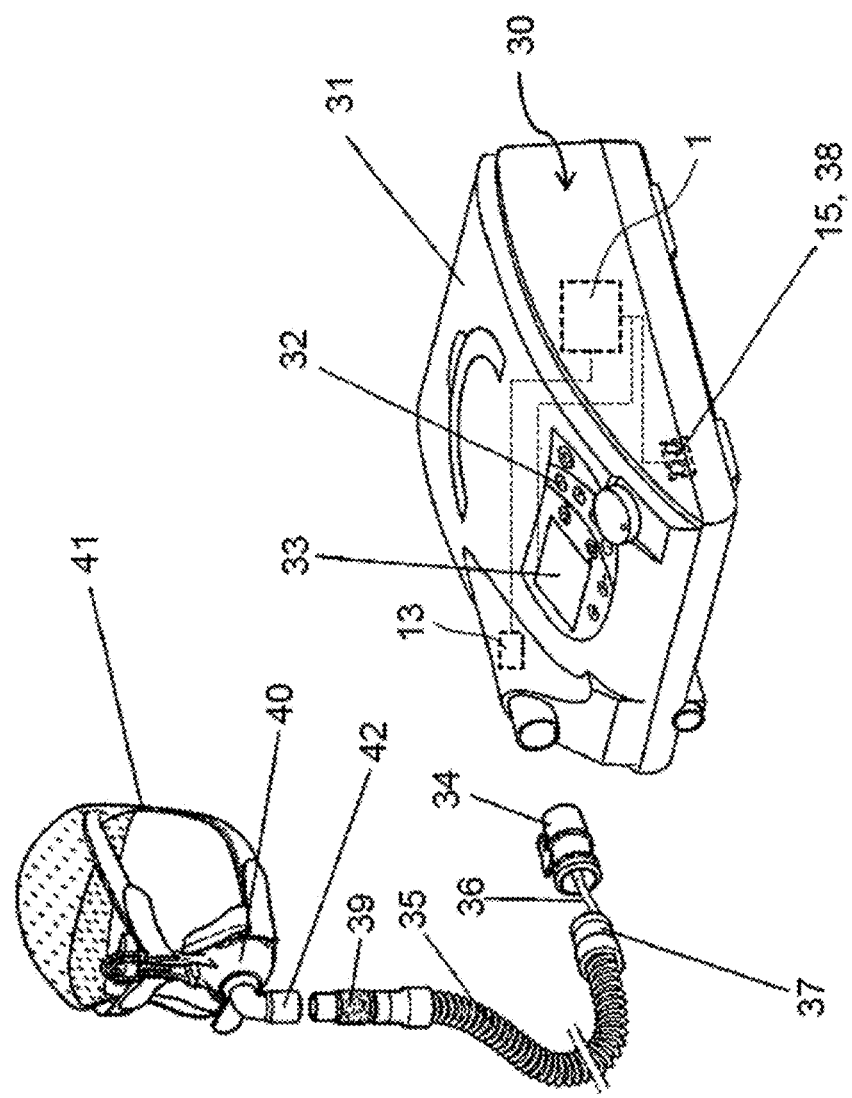
FIG. 8 shows a perspective view of an illustrative embodiment of a ventilator according to the invention.

FIG. 8 shows a perspective view of an illustrative embodiment of a ventilator 30 for ventilating a person with a respiratory gas from a respiratory gas source (not shown), which can be arranged in an interior of an appliance housing 31, according to the invention. An operating element 32 and a display device 33 are provided in the region of the appliance housing 31, wherein the display device 33 can also be configured as a combined operating and display device, for example with a touch-sensitive input unit. A connection tube 35 is attached via a coupling 34. An additional pressure-measuring tube 36 can extend along the connection tube 35 and is connectable to the appliance housing 31 via a pressure inlet nozzle 37. To permit data transmission, the ventilator 30 has at least one, or a multiplicity of, data transmission interface(s) 15, 38.

In the ventilator 30 shown in FIG. 8, the breath analyzer 1 according to the invention shown in FIG. 1 is designed as part of the ventilator 30. As will also be seen from FIG. 8, the breath analyzer 1 is coupled to the sensor unit 13 shown in FIG. 1, assigned here to the ventilator 30, and coupled to the data transmission interfaces 15 or 38.

A humidifier (not shown) known per se can additionally be adapted. An exhalation element 39 is arranged in the region of an end of the connection tube 35 directed away from the appliance housing 31. An exhalation valve (not explicitly shown) can likewise be used.

FIG. 8 moreover shows a patient interface designed as a breathing mask 40, in the present case as a nasal mask. Headgear 41 can be used to attach the mask in the region of the head of a person who is to be ventilated. In the region of the end thereof facing the connection tube 35, the patient interface 40 has a coupling element 42.

The input and/or output of data, for example dead space volume, can for example be performed via the interface 38. The data transmission interface(s) 15, 38 can be implemented as wired, as an infrared interface, as a Bluetooth interface or as a USB. A card slot (not shown) is preferably also provided. The interface 15, can also be embodied as a LAN interface or as another data transmission interface for connection to a network, the Internet, etc. An oxygen supply valve (not shown) can be adapted to the ventilator 30 in the region of the appliance housing 31. It is conceivable to additionally enrich the respiratory gas with oxygen in order to improve the patient supply.

By way of the interfaces 38—for example embodied as a card slot or USB—it is also possible for data external to the therapy to be loaded into the ventilator 30 according to the invention or to be loaded from the latter into a data receiver external to the appliance. The user must confirm a query in the operating field 32 of the display device 33, if the ventilator 30 identifies external storage media, whereupon the data are selectively stored in the region of the ventilator 30 or executed.

Telemedical data can be input and/or output by way of the interface 38. For this purpose, for example, mobile wireless or short-range wireless data or WLAN or Bluetooth or network data are received/transmitted via the data transmission interface 38.

The ventilator 30 is designed such that it can be connected via the tube 35 and the patient interface 40 to the person or patient who is to be ventilated, in order to provide ventilation through the appliance 30. The respiratory gas source can be designed, for example, as an electric motor having a fan wheel driven by the latter (neither of them shown here). The sensor unit 13 is designed to determine the ventilation pressure and/or the respiratory flow and/or the tidal volume of the respiratory gas. The ventilator 30 has an electronic control unit (not shown) which is designed such that a respiratory gas pressure is determined for each breath on the basis of a predetermined value for the patient and/or on the basis of measurement signals of the sensor unit 13, and the respiratory gas source is regulated in such a way that the desired respiratory gas pressure or ventilation pressure is generated.

A particularly preferred field of use of the breath analyzer or of the breath analysis method disclosed herein is the monitoring of expiration phases of the ventilated person, for example during sleep. A number of complications arising in ventilation can be detected on the basis of the respiratory flow curve during expiration. By means of prompt reaction (for example by medication or by optimization of the ventilation settings), the outcome of the ventilation can be considerably improved.

Thus, the expiratory respiratory flow curve of the ventilated person can already be evaluated for example in the ventilator 30, if the latter has a corresponding evaluation unit, wherein preferably at least 2 of 4 complications are detected: severity of an expiratory flow limitation, severity of an intrinsic PEEP, frequency of missed breaths (absence of inspiration trigger, or ineffective inspiration effort), frequency of coughs. The detection of the respective breath classes from the determined signal segments can be effected, for example, by pattern recognition, comparison of the expiration curve with stored reference curves, evaluation of the respiratory flow and/or the increase of the respiratory flow or the exhaled volume at defined times during the course of expiration. Storage and processing of the detected complications can take place in the ventilator itself and/or be transmitted to a data receiver via the data transmission interface 38. Detected complications are preferably transmitted to a monitoring unit, for example in a hospital or nursing home, to a monitor, and, in the case of ventilation at home, to a telemonitoring server. In addition, a visual or acoustic indication or alarm can be triggered on the monitoring unit, if the frequency or the severity of the complications exceeds a fixed limit value.

In order to detect the aforementioned breathing events, the respiratory flow can in each case be evaluated during the expiration phase 17 of the ventilator 30, optionally in combination with the ventilation pressure, or with the speed of rotation, detected by the sensor unit 14 (FIG. 1), of a ventilator fan of the respiratory gas source, and/or with the detected leakage losses.

For each of the patterns or each of the aforementioned breathing events that are detectable in the expiration, there are different detection possibilities according to the invention. These can be applied individually or in combination and are also to be regarded only as examples. It is also not necessary to look for all of the described patterns, but at least for one.

The evaluation, for example by an evaluation unit provided inside the ventilator 30 or alternatively/additionally by an evaluation unit external to the appliance (neither evaluation unit shown), can include one or a combination of the following method steps:

a) evaluation of the expiratory flow amplitudes, in particular maxima and minima, and the time of their occurrence:
maximum during the first part of the expiration phase signifies: inspiration time too short, further inspiration efforts
maximum during the further course of the expiration phase signifies: missed breath
minimum lower than in preceding breaths signifies: cough
respiratory flow at start of inspiration still negative signifies: intrinsic PEEP b) evaluation of the expiratory volume and, if appropriate, of an inspiratory volume that is measurable during the expiration phase:
positive volume in a portion of the expiration phase signifies: missed breath
expiratory volume is increased in comparison with preceding expirations signifies: cough
expiratory volume lower than inspiratory volume signifies: intrinsic PEEP c) evaluation of the derivation (=gradient) of the respiratory flow:
rise followed by fall during the first part of the expiration phase signifies: inspiration time too short, further inspiration efforts
rise followed by fall during the further course of the expiration phase signifies: missed breath
fall steeper than in preceding breaths signifies: cough d) evaluation of the volume distribution of the exhalation during the expiration phase:
volume fractions especially at the start and at the end of a breath signifies: missed breath
volume fractions strongly bundled at the start of a breath signifies: intrinsic PEEP e) evaluation of the contour of the respiratory flow and/or of the volume curve:
correlation or other degree of similarity with stored or learned reference contour curves
pattern recognition, for example with neural networks or support vector machines or principal component analysis or fuzzy logic Instead of the evaluation, described herein, of the respiratory flow over time, it is alternatively also possible to evaluate the respiratory flow and/or the tidal volume via the ventilation pressure (P/V diagram).

The breath analyzer disclosed herein according to the invention, the ventilator, and the method according to the invention for breath analysis are not limited to the respectively disclosed embodiments but instead also comprise further embodiments of equivalent function which arise from technically feasible further combinations of the described features of the breath analyzer, of the ventilator, and of the breath analysis method. In particular, the features and feature combinations cited above in the general description and in the description of the figures, and/or shown merely in the figures, may be used not only in the combinations as explicitly given herein but also in other combinations or alone, without departing from the context of the present invention.

In a preferred embodiment, the breath analyzer according to the invention is used in a ventilator in order to automatically detect different breathing events of a person ventilated with a respiratory gas by the ventilator, for example during sleep, and to make these available for subsequent processing, as described herein.

To sum up, the present invention provides:

1. A breath analyzer for the detection of breathing events of a person ventilated with a respiratory gas, wherein the breath analyzer comprises an electronic computing and storage unit (2) which is designed and configured to receive a signal (3) corresponding to a ventilation pressure and/or a respiratory flow and/or a tidal volume of the respiratory gas delivered to the person and, during a predetermined analysis duration, to detect a curve of the signal (3) by means of a curve analyzer (4), the computing and storage unit (2) being designed and configured to determine from the signal curve a signal segment (5) which, on the basis of a predefined segment duration (6) or a segment duration (6) detected from the signal curve, is set shorter than the analysis duration, and to assign the determined signal segment (5) by means of a comparator (7) to one of several breath classes and in each case to store a frequency of occurrence, of the breath class assigned during the analysis duration, in a frequency counter (8) provided for each breath class in the storage unit (2), and to store at least one of the signal segments (5) determined during the analysis duration, but fewer than the frequency of occurrence detected in the frequency counter (8), for each assigned breath class in the storage unit (2, 9).
2. The breath analyzer of item 1, wherein the computing and storage unit (2) is designed and configured to store, for each breath class, only a predetermined maximum number of signal segments (5) in the storage unit (2, 9).
3. The breath analyzer of item 1 or item 2, wherein the number of the plurality of signal segments (5) to be stored can be fixed separately for at least two different breath classes.
4. The breath analyzer of any one of the preceding items, wherein the segment duration (6) of the signal segment (5) can be fixed on the basis of at least one predetermined signal curve criterion which is selected from gradient and/or a gradient profile of the signal curve, and occurrence of a maximum and/or minimum of the signal curve.
5. The breath analyzer of any one of the preceding items, wherein the segment duration (6) is dimensioned such that the signal segment (5) contains at least one complete breath, preferably 1 to 3 breaths, or at least 3 to a maximum of 10 breaths.
6. The breath analyzer of any one of the preceding items, wherein the stored signal segment (5) is provided with a time stamp of its determination.
7. The breath analyzer of any one of the preceding items, wherein the comparator (7) is designed and configured to assign the signal segment (5) to the breath class by means of pattern recognition, and/or by means of a comparison of the signal curve in the signal segment (5) with a predetermined number of predefined reference signal curves (10) stored beforehand in the storage unit (2), and/or by means of a detected gradient and/or a gradient profile of the signal curve in the signal segment (5), and/or by means of one or more detected maxima and/or minima of the signal curve in the signal segment (5).
8. The breath analyzer of any one of the preceding items, wherein the comparator (7) is designed and configured to store a predetermined number of selected signal segments (5), assigned to the breath classes during the analysis duration, as newly added, adaptively learned reference signal curves (11) in the storage unit (2), and to take these into consideration when assigning future detected signal segments (5) to the breath classes.
9. The breath analyzer of any one of the preceding items, wherein the breath classes include the breath types inspiration, expiration, pause and cough, preferably in addition also breath types which represent an inspiratory flow limitation and/or an expiratory flow limitation and/or an intrinsic PEEP 20, and/or breath asynchrony types such as ineffective breathing effort 18 and/or a double breathing effort (double triggering) 19.
10. The breath analyzer of any one of the preceding items, wherein the breath class ineffective breathing effort 18 is detected by the fact that the respiratory flow during the expiration phase 17 is analyzed, and the respiratory flow during the expiration phase 17 has at least intermittently a sign reversal.
11. The breath analyzer of any one of the preceding items, wherein the breath class ineffective breathing effort 18 is detected by analyzing whether the exhalation flow within a first time window at the start of expiration exceeds a defined threshold (e.g. in 1/min) and thereafter decreases within a second time window until it falls below a certain threshold or there is even briefly a positive, i.e. inspiratory, respiratory flow or at least the derivation of the respiratory flow points to a decrease of the expiratory respiratory flow, wherein a check is then made as to whether the exhalation flow increases again within a third time window, i.e. there is once again a stronger exhalation flow, or at least the derivation of the respiratory flow points to a renewed increase of the expiratory respiratory flow, even before the next inspiration is detected.
12. The breath analyzer of any one of the preceding items, wherein the breath class ineffective breathing effort 18 is detected by virtue of the fact that the ineffective inspiration effort 18 is detected by a pattern recognition which compares the curve of the respiratory flow with previously stored test patterns that represent ineffective inspiration efforts.
13. The breath analyzer of any one of the preceding items, wherein the breath class double triggering 19 is detected by comparing the exhalation time with a multiplicity of preceding (typical) exhalation times or with an average exhalation time or a predefined exhalation time.
14. The breath analyzer of any one of the preceding items, wherein the breath class double triggering 19 is detected by comparing the measured flow with a theoretical respiratory flow, wherein the measured flow remains high in relation to the theoretical respiratory flow after switching to expiratory ventilation pressure.
15. The breath analyzer of any one of the preceding items, wherein the detection of the breath class intrinsic PEEP 20 is effected on the basis of stored exemplary curve profiles of flow or volume which are representative of an intrinsic PEEP 20, current curve profiles being for this purpose compared with the stored curve profiles.

16. The breath analyzer of any one of the preceding items, wherein the detection of the breath class intrinsic PEEP 20 is effected by an evaluation of the temporal flow or volume distribution within the expiration, at the start of the expiration a high exhalation flow being detected which then decreases and, in the further course of the expiration, transitioning into a low exhalation flow.

17. The breath analyzer of any one of the preceding items, wherein the detection of the breath class intrinsic PEEP 20 is effected by a detection of an inspiration effort 18 of the patient and an evaluation of the exhalation flow in the time range of the inspiration effort 18, the remaining expiratory respiratory flow in the time range of the initiation of the next inspiration phase being representative of the extent of the intrinsic PEEP.

18. The breath analyzer of any one of the preceding items, wherein the detection of the breath class cough 21 is effected by pattern recognition of the expiration curve of flow or volume on the basis of stored curves which are representative of coughs, current curves being for this purpose compared with the stored curves.

19. The breath analyzer of any one of the preceding items, wherein the detection of the breath class cough 21 is effected by comparing the curve of the current exhalation flow, the peak exhalation flow or peak exhalation volume with the typical preceding exhalation flows, peak exhalation flows or peak exhalation volumes of the patient for the detection of a forced exhalation that points to a cough, a cough being detected when the current breath reaches over about 70% or over about 140% or over about 200% of the typical breaths.

20. The breath analyzer of any one of the preceding items, wherein the comparator (7) is designed and configured to receive additional information concerning the breath type, such as spontaneous or mandatory breathing, and/or concerning a speed of rotation of a ventilation fan delivering the respiratory gas to the person, and/or concerning a leakage loss of the respiratory gas delivered to the person, and to take this additional information into account when assigning the signal segment (5) to the breath classes.

21. A ventilator for ventilating a person with a respiratory gas, wherein the ventilator comprises a sensor unit (13) for determining a ventilation pressure and/or a respiratory flow and/or a tidal volume of the respiratory gas delivered to the person, and further comprises the breath analyzer (1) of any one of the preceding items, the sensor unit (13) being coupled in a data-transmitting manner to the computing and storage unit (2) of the breath analyzer (1) and being configured to generate a signal (3) corresponding to the determined ventilation pressure and/or to the determined respiratory flow and/or to the determined tidal volume of the respiratory gas and to deliver this signal to the computing and storage unit (2).

22. The ventilator of item 21, wherein at least one data transmission interface (15, 38) which is designed and configured to transmit to a data receiver unit the content, stored in the storage unit (2), of the frequency counter (8) of each breath class and/or the at least one signal segment (5), stored in the storage unit (2, 9), of each assigned breath class.

23. The ventilator of item 21 or item 22, wherein a further sensor unit (14) is provided and designed to detect a speed of rotation of a ventilation fan and/or a leakage loss of the respiratory gas during the ventilation of the person and/or a breath type such as spontaneous breathing or mandatory breathing, and to deliver this to the breath analyzer (1).

24. The ventilator of any one of items 21 to 23, wherein an evaluation unit which is designed and configured to evaluate the analysis result of the breath analyzer (1) in terms of health-critical complications of the ventilated person and to store it in the storage unit (2) and/or display it on a display device (33) and/or transmit it to an external data receiver unit.

25. The ventilator of any one of items 21 to 24, wherein, upon detection of an inspiratory flow limitation and/or an expiratory flow limitation and/or an intrinsic PEEP 20 and/or an ineffective breathing effort 18 and/or a double breathing effort (double triggering) 19, at least one message is output via the data transmission interface and/or on the display or is stored in data.

26. The ventilator of any one of items 21 to 25, wherein, upon detection of an inspiratory flow limitation and/or an expiratory flow limitation and/or an intrinsic PEEP 20 and/or an ineffective breathing effort 18 and/or a double breathing effort (double triggering) 19, at least one setting of the ventilation is changed, the setting being selected from IPAP and/or EPAP and/or inspiration time and/or expiration time and/or trigger sensitivity.

27. A method for detecting breathing events of a person ventilated with a respiratory gas, in which method a signal (3) corresponding to a ventilation pressure and/or a respiratory flow and/or a tidal volume of the respiratory gas delivered to the person is generated by means of a sensor unit (13) and, during a predetermined analysis duration, a time curve of the signal (3) is determined, a signal segment (5) being determined from the signal curve, which signal segment (5), on the basis of a predefined segment duration (6) or a segment duration (6) detected from the signal curve, is set shorter than the analysis duration, and the determined signal segment (5) being assigned to one of several breath classes, wherein in each case a frequency of occurrence, of the breath class assigned during the analysis duration, is stored in a frequency counter (8) provided for each breath class, and at least one of the signal segments (5) determined during the analysis duration, but fewer than the frequency of occurrence detected in the frequency counter (8), is stored for each assigned breath class.

What is claimed is:

1. A breath analyzer for the detection of breathing events of a person ventilated with a respiratory gas, wherein the breath analyzer comprises an electronic computing and storage unit which is configured to receive a signal corresponding to a ventilation pressure and/or a respiratory flow and/or a tidal volume of the respiratory gas delivered to the person and, during a predetermined analysis duration, to detect a curve of the signal by a curve analyzer, the computing and storage unit being configured to determine from the signal curve a signal segment which, on the basis of a predefined segment duration or a segment duration detected from the signal curve, is set shorter than an analysis duration, and to assign the determined signal segment by a comparator to one of several breath classes and in each case to store a frequency of occurrence, of the breath class assigned during the analysis duration, in a frequency counter provided for each breath class in the computing and storage unit and to store at least one of the signal segments determined during the analysis duration, but fewer than a frequency of occurrence detected in the frequency counter, for each assigned breath class in the computing and storage unit.

2. The breath analyzer of claim 1, wherein the computing and storage unit is configured to store, for each breath class, only a predetermined maximum number of signal segments.

3. The breath analyzer of claim 1, wherein the analyzer is capable of fixing a number of a plurality of signal segments to be stored separately for at least two different breath classes.

4. The breath analyzer of claim 1, wherein the analyzer is capable of fixing the segment duration of the signal segment on the basis of at least one predetermined signal curve criterion selected from gradient and/or gradient profile of the signal curve, and occurrence of a maximum and/or minimum of the signal curve.

5. The breath analyzer of claim 1, wherein the segment duration is dimensioned such that the signal segment contains at least one complete breath.

6. The breath analyzer of claim 1, wherein the stored signal segment is provided with a time stamp of its determination.

7. The breath analyzer of claim 1, wherein the comparator is configured to assign the signal segment to a breath class by pattern recognition and/or by a comparison of the signal curve in the signal segment with a predetermined number of predefined reference signal curves stored beforehand in the computing and storage unit and/or by a detected gradient and/or a gradient profile of the signal curve in the signal segment and/or by one or more detected maxima and/or minima of the signal curve in the signal segment.

8. The breath analyzer of claim 1, wherein the comparator is configured to store a predetermined number of selected signal segments, assigned to breath classes during the analysis duration, as newly added, adaptively learned reference signal curves in the computing and storage unit, and to take these curves into consideration when assigning future detected signal segments to the breath classes.

9. The breath analyzer of claim 1, wherein the breath classes include the breath types inspiration, expiration, pause and cough.

10. The breath analyzer of claim 9, wherein the breath classes additionally include breath types which represent an inspiratory flow limitation and/or an expiratory flow limitation and/or an intrinsic positive end-expiratory pressure (PEEP), and/or ineffective breathing effort and/or a double breathing effort.

11. The breath analyzer of claim 10, wherein the breath class ineffective breathing effort is detected by the fact that the respiratory flow during an expiration phase is analyzed, and a respiratory flow during the expiration phase shows at least intermittently a sign reversal, or is detected by analyzing whether the exhalation flow within a first time window at a start of expiration exceeds a defined threshold and thereafter decreases within a second time window until it falls below a certain threshold or there is briefly a positive respiratory flow or at least the derivation of the respiratory flow points to a decrease of the expiratory respiratory flow, a check being then made as to whether the exhalation flow increases again within a third time window, or at least a derivation of the respiratory flow points to a renewed increase of the expiratory respiratory flow, even before the next inspiration is detected, or is detected by virtue of the fact that the ineffective inspiration effort is detected by a pattern recognition which compares the curve of the respiratory flow with previously stored test patterns that represent ineffective inspiration efforts.

12. The breath analyzer of claim 10, wherein the breath class double triggering is detected by comparing the exhalation time with a multiplicity of preceding exhalation times or with an average exhalation time or a predefined exhalation time, or is detected by comparing a measured flow with a theoretical respiratory flow, the measured flow remaining high in relation to a theoretical respiratory flow after switching to expiratory ventilation pressure.

13. The breath analyzer of claim 10, wherein detection of the breath class intrinsic PEEP is effected on the basis of stored exemplary curve profiles of flow or volume which are representative of an intrinsic PEEP, current curve profiles being for this purpose compared with the stored curve profiles, or is effected by an evaluation of a temporal flow or volume distribution within an expiration, at the start of the expiration a high exhalation flow being detected which then decreases and, in the further course of the expiration, transitioning into a low exhalation flow, or is effected by a detection of an inspiration effort of the patient and an evaluation of an exhalation flow in a time range of the inspiration effort, the remaining expiratory respiratory flow in the time range of the initiation of the next inspiration phase being representative of an extent of the intrinsic PEEP.

14. The breath analyzer of claim 9, wherein the detection of the breath class cough is effected by pattern recognition of the expiration curve of flow or volume on the basis of stored curves which are representative of coughs, current curves being for this purpose compared with the stored curves, or is effected by comparing the curve of the current exhalation flow, the peak exhalation flow or peak exhalation volume with typical preceding exhalation flows, peak exhalation flows or peak exhalation volumes of the patient for detection of a forced exhalation that points to a cough, a cough being detected when a current breath reaches over about 70% of typical breaths.

15. The breath analyzer of claim 1, wherein the comparator is configured to receive additional information concerning the breath type and to take this additional information into account when assigning the signal segment to the breath classes.

16. A ventilator for ventilating a person with a respiratory gas, wherein the ventilator comprises a sensor unit for determining a ventilation pressure and/or a respiratory flow and/or a tidal volume of the respiratory gas delivered to the person, and further comprises the breath analyzer of claim 1, the sensor unit being coupled in a data-transmitting manner to the computing and storage unit of the breath analyzer and being configured to generate a signal corresponding to a determined ventilation pressure and/or to a determined respiratory flow and/or to a determined tidal volume of the respiratory gas and to deliver this signal to the computing and storage unit.

17. The ventilator of claim 16, wherein there is provided at least one data transmission interface which is configured to transmit to a data receiver unit a content, stored in the computing and storage unit, of the frequency counter of each breath class and/or the at least one signal segment, stored in the computing and storage unit, of each assigned breath class.

18. The ventilator of claim 16, wherein a further sensor unit is provided and designed to detect a speed of rotation of a ventilation fan and/or a leakage loss of the respiratory gas during the ventilation of the person and/or a breath type, and to deliver this to the breath analyzer.

19. The ventilator of claim 16, wherein the ventilator further comprises an evaluation unit which is configured to evaluate an analysis result of the breath analyzer in terms of health-critical complications of the ventilated person and to store it in the storage unit and/or display it on a display device (33) and/or transmit it to an external data receiver unit.

20. A method for detecting breathing events of a person ventilated with a respiratory gas, wherein the method comprises generating a signal corresponding to a ventilation pressure and/or a respiratory flow and/or a tidal volume of the respiratory gas delivered to the person by a sensor unit and, during a predetermined analysis duration, determining a time curve of the signal, determining a signal segment from the signal curve, which setting the signal segment, on the basis of a predefined segment duration or a segment duration detected from the signal curve, shorter than an analysis duration, assigning the determined signal segment to one of several breath classes, storing in each case a frequency of occurrence, of the breath class assigned during the analysis duration, in a frequency counter provided for each breath class, and storing at least one of the signal segments determined during the analysis duration, but fewer than the frequency of occurrence detected in the frequency counter, for each assigned breath class.

\* \* \* \* \*